United States Patent
Flugger

(10) Patent No.: US 6,936,000 B2
(45) Date of Patent: *Aug. 30, 2005

(54) PROCESS AND APPARATUS FOR SELECTING OR DESIGNING PRODUCTS HAVING CONTENT-FREE SOUND OUTPUTS

(75) Inventor: Ray T. Flugger, Forestville, CA (US)

(73) Assignee: Flowmaster, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/444,429

(22) Filed: May 23, 2003

(65) Prior Publication Data

US 2003/0220537 A1 Nov. 27, 2003

Related U.S. Application Data

(63) Continuation of application No. 09/766,016, filed on Jan. 22, 2001, now Pat. No. 6,584,346.

(51) Int. Cl.[7] .................... A61M 21/00; A61B 5/04; G06F 19/00

(52) U.S. Cl. ............... 600/28; 600/544; 702/33

(58) Field of Search ................. 600/544, 545, 600/27, 28, 390; 702/33; 703/8; 705/10; 364/413.05, 236, 419; 128/731, 745; 351/210; 434/238; 354/62; 984/301

(56) References Cited

U.S. PATENT DOCUMENTS

| | | | |
|---|---|---|---|
| 4,483,681 A | 11/1984 | Weinblatt | |
| 4,528,989 A | 7/1985 | Weinblatt | |
| 4,789,235 A | 12/1988 | Borah et al. | |
| 5,243,517 A | 9/1993 | Schmidt et al. | |
| 5,662,117 A | 9/1997 | Bittman | |
| 6,334,068 B1 | 12/2001 | Hacker | |
| 6,584,346 B2 * | 6/2003 | Flugger | 600/544 |

* cited by examiner

Primary Examiner—Max F. Hindenburg
Assistant Examiner—Nikita R. Veniaminov
(74) Attorney, Agent, or Firm—Dorsey & Whitney LLP

(57) ABSTRACT

A process and apparatus for selecting or designing a product, such as a muffler, having a complex, content-free sound output which is less stressful or more pleasing. The process includes the steps of sensing at least one physiological response of a subject (21) while the subject listens to an initial content-free sound output, repeating the sensing step for a new content-free sound output, comparing the physiological responses, and selecting the sound output for use in selecting or designing the product which output produces the physiological response that is the least stressful or most pleasing to the subject. The apparatus includes an audio playback device (15), a sound recording (16) of the initial sound, a sound recording (16) of the new sound, and physiological monitoring apparatus (17) suitable for attachment to and monitoring of the physiological responses of the test subject (21) to the playback of the sound recordings.

12 Claims, 4 Drawing Sheets

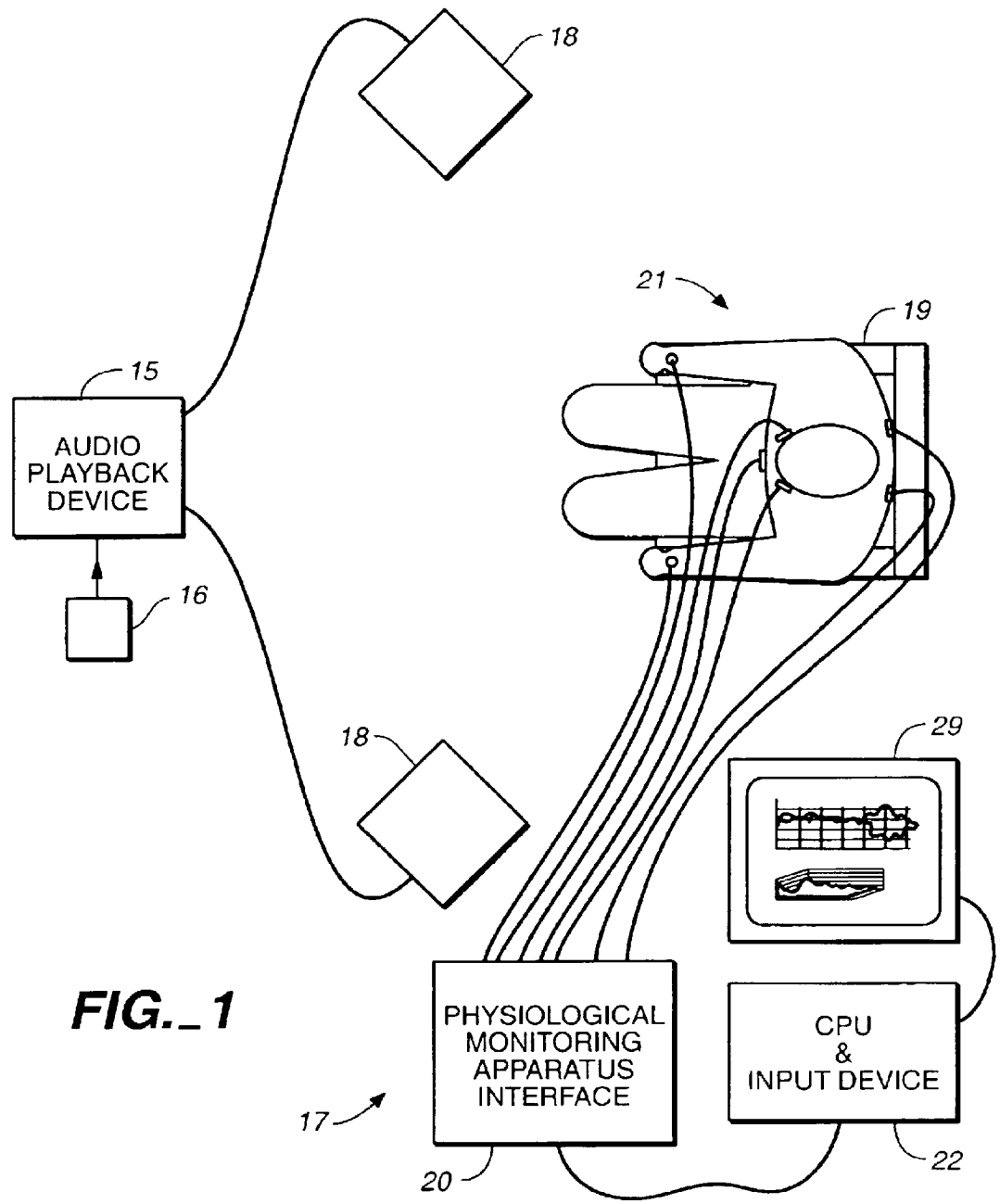
FIG._1

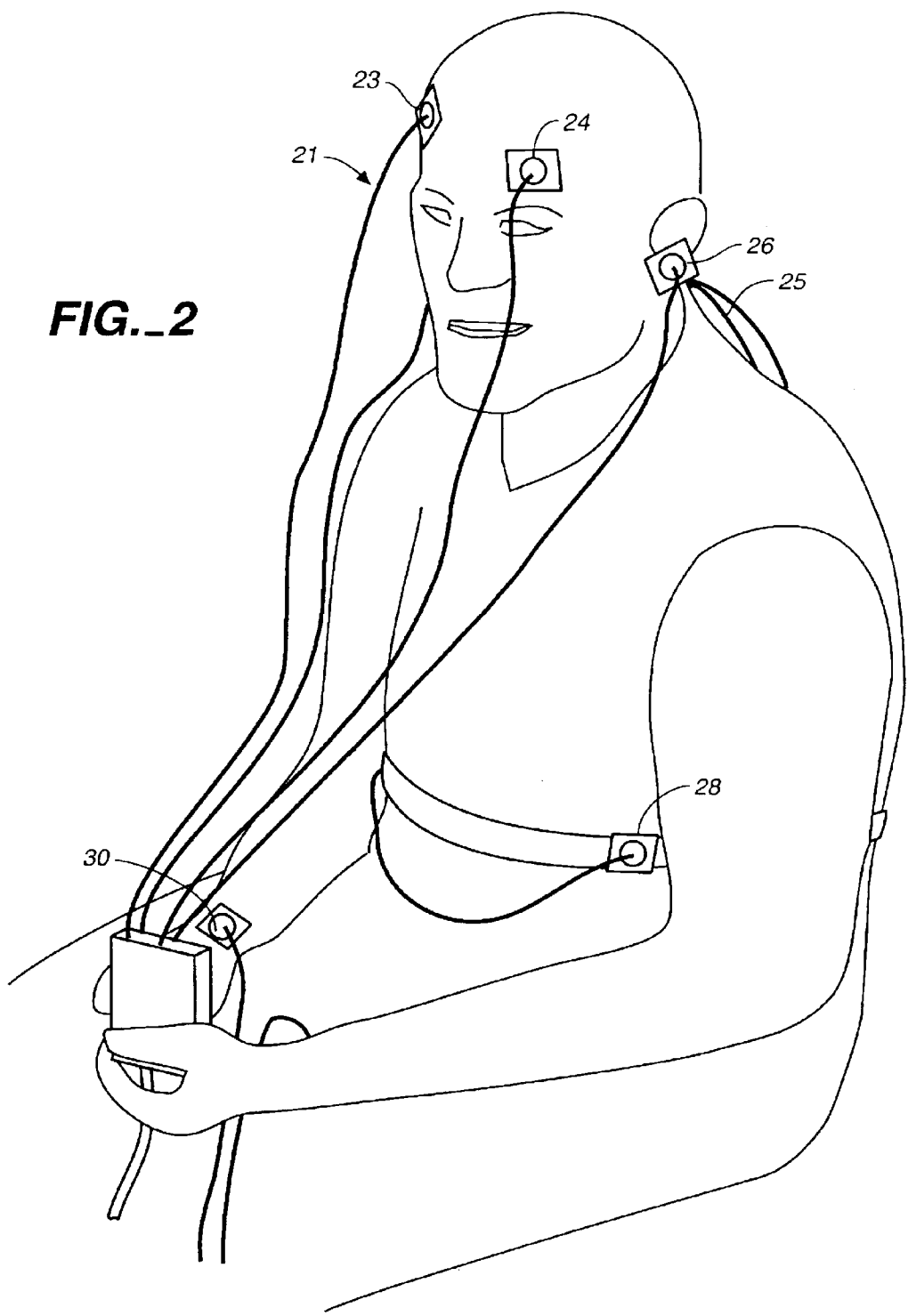
FIG._2

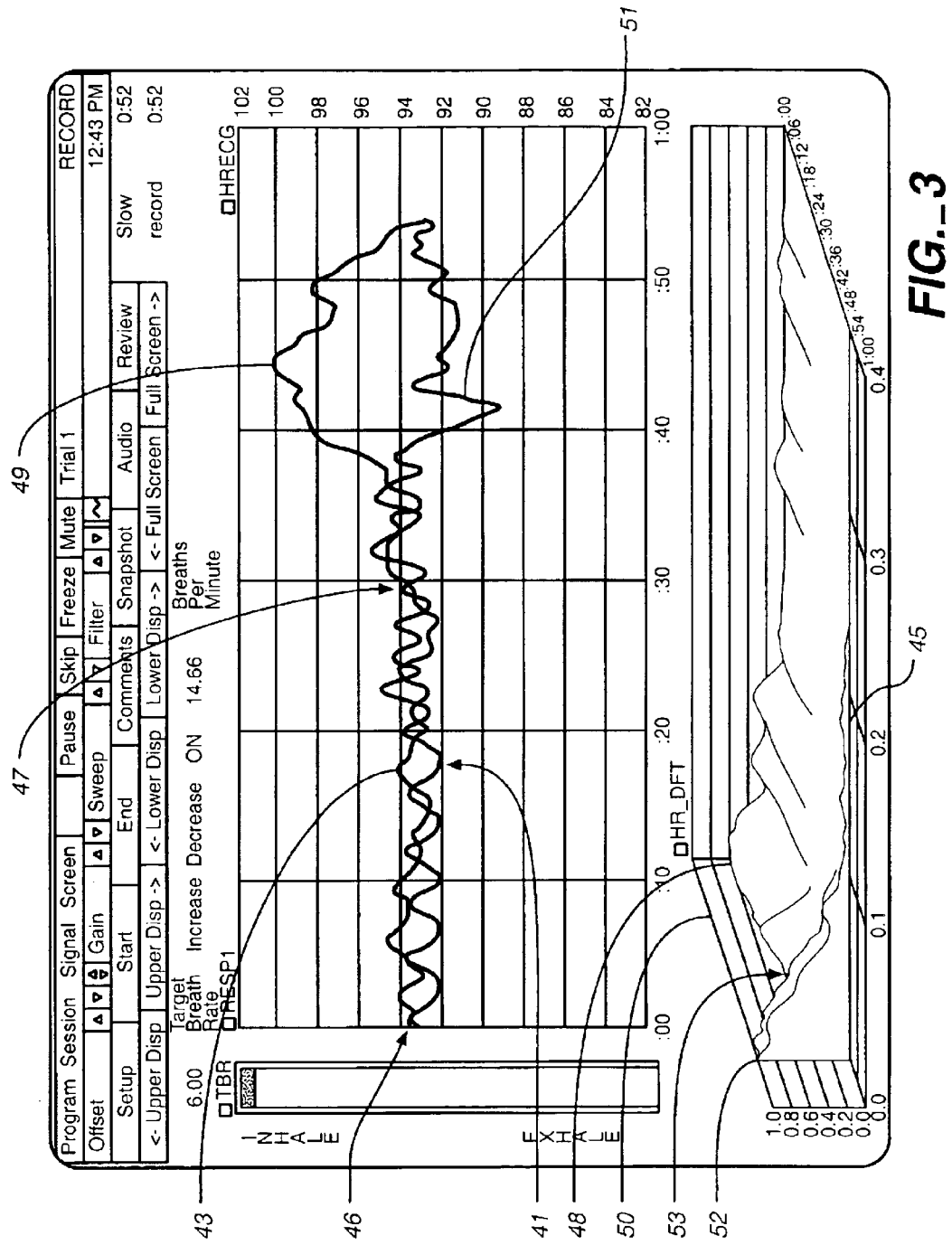
FIG._3

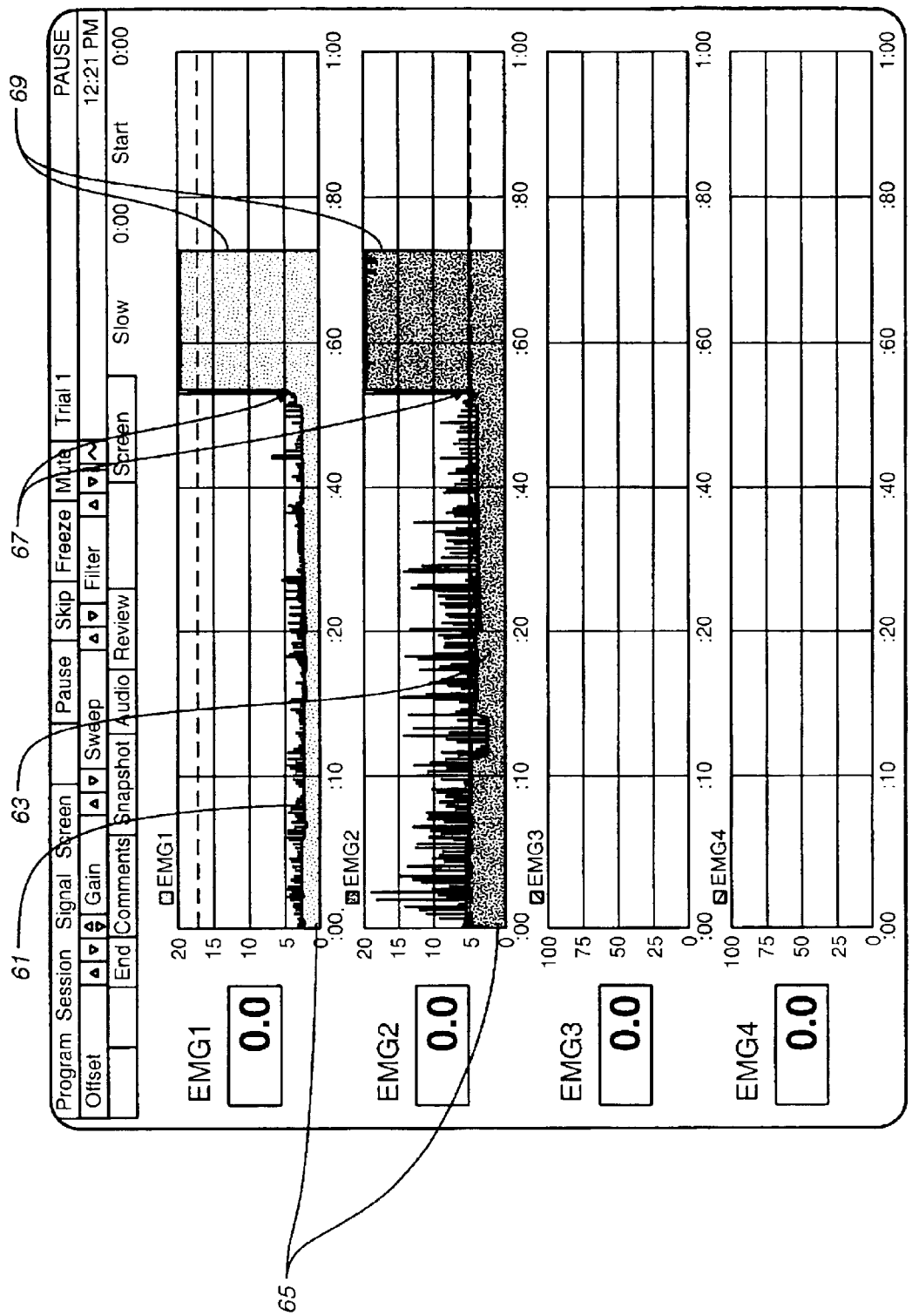
FIG._4

PROCESS AND APPARATUS FOR SELECTING OR DESIGNING PRODUCTS HAVING CONTENT-FREE SOUND OUTPUTS

RELATED APPLICATION

This application is a continuation application based upon application Ser. No. 09/766,016 filed Jan. 22, 2001 now U.S. Pat. No. 6,584,346 and entitled PROCESS AND APPARATUS FOR SELECTING OR DESIGNING PRODUCT HAVING SOUND OUTPUTS.

FIELD OF THE INVENTION

The present process and apparatus relate, in general, to the study of human responses to external stimuli such as light, vibration and sound and, more particularly, relate to the physiological responses of a human to sound stimuli and the use of such responses to test, select and/or design products which produce less stress or have a more pleasing sound output.

BACKGROUND ART

The study of the physiological response of a human to various sounds has increased in recent years. The effects of music, for example, on humans of various ages has been studied using sophisticated electrophysiological monitoring apparatus, such as electroencephalographs, electrocardiographs, electromyographs and even MRI scanners. Attempts have been made, for example, to determine whether or not music has a positive effect on the functioning of the brain while performing tasks such as mathematical problems.

In the industrial arena noise, vibration and harshness (NVH) effects have been studied in the automotive field. The general approach to such studies has been to try to isolate, eliminate or reduce the NVH level in automobiles so that the user does not have to endure long periods of time during which he or she is exposed to NVH levels that cause fatigue, irritability and/or drowsiness.

Studies directed to the effects of sound on humans also have included subjective approaches. Thus, panels or juries are asked to subjectively rank sound quality as between categories, such as, rough, sharp, metallic, whiney and hollow. Using such subjective rankings by panels of listeners the goal has been to try to predict sound-quality preferences, that is, to try to quantify in some manner the subjective impressions of the panel.

In some cases it is possible to simply isolate the user from the sound output, but in many cases such isolation is not practical or even possible. Moreover, in some instances, the sound output of a product can actually be pleasing, or made to be more pleasing. Thus, it has been a common experience in connection with mufflers for internal combustion engines that some mufflers will attenuate sound in a manner which is effective as to the decibel level, but nevertheless is irritating, stressful or unpleasant. Other mufflers, by contrast, are known to be subjectively more pleasing to the driver. Exactly why one muffler is annoying, while the other is pleasing, is only known in a general subjective sense, namely, that one has a harmony of sound or a consonance which is more appealing to the driver and to persons past whom the vehicle is driven.

Sound output which has intellectually perceivable sound content, such as advertising, also has been studied by sensing electrophysiological responses of subjects. Thus, in U.S. Pat. No. 5,243,517, subjects listen to a plurality of proposed advertisements having different intellectually perceivable content and their physiological responses to the changed advertisements are sensed. The subjects' physiological responses to content changes were then used to select as between advertisements.

Accordingly, it is an object of the present invention to provide a process and apparatus for selecting or designing products, such as exhaust mufflers for internal combustion engines or other products having content-free sound outputs, which resulting products produce an objectively demonstratable lessened mobilization of the body's stress response mechanisms, or a more pleasing physiological response in humans.

A further object of the present invention is to provide a process and apparatus for producing or choosing a product having a multi-frequency, content-free sound output in which electrophysiological monitoring techniques are employed to objectively enhance product design or selection.

The process of the present invention has other objects and features which are set forth in, or will be apparent from, the following Best Mode of Carrying Out the Invention and the accompanying drawing.

DISCLOSURE OF THE INVENTION

The process and apparatus of the present invention is used to test and select or design a product having a content-free sound output which produces less stress and therefore is more pleasing to a human listener. Briefly, the process comprises the steps of: sensing at least one physiological response of a subject while the subject listens to an initial content-free sound output; changing at least one of the frequencies present in the initial sound output to produce a new content-free sound output; repeating the sensing step for the new sound output; comparing the physiological response for the initial sound output with the physiological response for the new sound output; and selecting the sound output for use in choosing as between products or for use in designing a product, which selected sound output produces one of: a lower physiological stress response or a higher physiological pleasure response in the subject. The sensing step preferably is accomplished by sensing a physiological stress response of the subject using apparatus, such as a surface electromyography monitoring apparatus, a pulse sensor, a respiratory rate sensor, and/or combinations of such physiological response sensors. In apparatus which have complex, multi-frequency, content-free sound outputs, such as exhaust system mufflers, the changing and sensing steps are repeated many times to produce a plurality of new sound outputs, which outputs each are compared prior to performing the step of selecting the least stressful or most pleasing content-free sound output.

The apparatus of the present invention comprises, briefly, an audio playback device, audio recordings of at least two content-free sounds from products of different designs to be tested, and a physiological monitoring apparatus formed to be attached to a subject for monitoring the physiological response of the subject when listening to playback of the various audio recordings.

BRIEF DESCRIPTION OF THE DRAWINGS

FIG. 1 is a top plan, schematic representation of apparatus constructed in accordance with the present invention.

FIG. 2 is a test subject with respiration, heart rate, muscle activity and brainwave activity sensors placed to sense the physiological response of the subject to sound stimuli.

FIG. 3 is a computer display screen showing variation of the respiration rate, pulse rate, and heart rate variability for the subject of FIG. 2 while listening to sound outputs for two mufflers.

FIG. 4 is a computer display of a surface electromyography monitoring apparatus output for the subject of FIG. 2 while the subject listens to the sound output of same two mufflers as tested in FIG. 3.

BEST MODE OF CARRYING OUT THE INVENTION

The sound output from an internal combustion engine, which sound output is free of any intelligible content or intellectual communication, is very difficult to completely isolate from the driver and passengers of a vehicle. It is even less practical to isolate engine exhaust sound output from people outside the vehicle. Exhaust mufflers are highly effective in reducing the decibel level to a level that can be tolerated by humans, but there can be a wide range in the quality of the sound of internal combustion engines as a result of muffler design. The attenuated sound output from a muffled internal combustion engine is a very complex, multi-frequency, content-free sound output which can be varied substantially through changes in muffler construction. For example, mufflers which employ internal baffles or partitions to attenuate sound can have the sound output changed substantially by shifting the position of the internal baffles by even fractions of an inch, or by changing the size of the attenuating chambers within the mufflers.

This tuning of muffler sound output has been done by muffler manufacturers for many years with varying success. The resulting muffler design is usually based upon a combination of objective criteria, such as reduction of the decibel level of the muffler, and subjective criteria, such as the sound found to be most pleasing to the ear of the design engineers or a Beta test panel. Since most manufacturers do not seek to have sound output from their mufflers which is harsh or disconsonant, the general goal is to attempt to achieve a pleasing sound result. Nevertheless, the sound output of mufflers from manufacturer to manufacturer varies widely because of the widely differing subjective view of what sound output is a "pleasing" sound, particularly since the sound output contains no perceivable content or objectively discernible communicated message.

One of the difficulties in connection with muffler tuning is that the complex, multi-frequency, content-free sound output will vary substantially when even small changes are made. Moreover, it is usually not practical to isolate a single frequency and remove it from muffler sound output. Thus, a structural change in the muffler will change many frequency components in the sound output, and it is almost impossible to change one or two frequencies at any time. Nevertheless, most manufacturers are aware of the ability, for example, to affect muffler sound output in certain bandwidths by structural changes. Low frequency sound components, for example, can be emphasized or reduced, as can high frequency sound components. Which bandwidths of content-free sound are more pleasing to the user's ears, and therefore should be emphasized, however, is still the subject of considerable dispute.

A further complication of muffler design is that muffler sound frequencies change with engine RPM. Thus, a muffler which has a pleasing sound output at idling engine speeds may become disconsonant and extremely stressful or irritating at full acceleration. Since it is not practical to change muffler geometry with engine speed, certain compromises have to be made. It still would be highly desirable, however, to be able to objectively compare the physiological responses of humans to the complex, content-free muffler sound outputs over the range of engine operating speeds so that the best, namely, the most pleasing or the least stressful, full range sound output could be achieved.

It has been found in the present invention that objective, physiological comparisons of the responses of a human to various complex, content-free sounds, such as a muffled internal combustion engine output, can be made. Once made, the sensed physiological responses can be used to design or select as between mufflers or other products so that they have a more agreeable sound output.

The brain processes sensory input, including sound input, and produces brain signals that can profoundly affect body functions. Harsh or disconsonant sound can cause stress or, even pain, while harmonious sound can produce pleasure. Both brain responses, stress and pleasure, are manifested by physiological responses. Thus, responsive stress and pleasure brain signals are sent to the nervous, pulmatory, circulatory and muscular systems when sound stimuli are perceived. The stress responses produced by the brain signals, however, are somewhat more easily monitored than the pleasure responses. For example, commonly experienced physiological responses to activating mobilization produced by the sympathetic nervous system are sensations such as pressure or tightness in the chest, blood rushing to the head, and a narrowing of awareness.

The ideal physiological sensing apparatus for use in the process of the present invention may well be apparatus which is capable of directly sensing physiological pleasure responses. A multi-transducer electroencephalograph of the type currently used in sophisticated laboratory settings, for example, is believed to be suitable for use with the process of the present invention, but it requires substantial computing power and the tedious attachment of many sensing transducers to the subject. Attempts to produce objective pleasure-based data using encephalographic brain monitoring apparatus with a pair of transducers and a laptop computer, however, have thus far not been sophisticated enough to yield useful data. Demonstratably reproducible objective data has been achieved, however, for sound-induced physiological stress responses. These stress-based data can be used to enable the selection or design of products which will produce less stressful, and therefore more pleasing, sound outputs.

Referring now to FIG. 1 the apparatus of the present invention can be seen to include three components, namely, an audio playback device 15, an audio recording 16 and a physiological monitoring apparatus, generally designated 17. Audio playback device 15 can be a compact disc player, tape deck or similar apparatus, which usually will have a plurality of speakers 18, or headphone (not shown), which is positioned to produce a highly realistic or accurate sound reproduction that can be listened to by a test subject 21, usually seated in a chair 19.

Sound recording 16 can be a disc, tape or other audio recording which is compatible with player 15. Recorded on recording 16 will be at least one audio, and usually a plurality of, sound recordings of different content-free sounds produced by products of the type to be studied during the testing. As will be apparent, a plurality of recordings 16 each have a single sound recorded on them also could be used. Recording 16 can contain, for example, two recordings of exhaust mufflers of differing geometry which have been attached to the exhaust system of the same engine. The first muffler will produce what can be identified as an "initial sound output," while the second muffler produces a "new sound output." The recording also could be two recordings of the same muffler, but with a changed or varied muffler geometry so as to produce the initial sound output and the new sound output. Obviously, recording 16 also could have more than two, changed or varied sound output recordings of products of the same type which produce somewhat differing content-free sound outputs.

In the broadest aspect of the process of the present invention there need not be an audio playback device or sound recording. Instead, subject 21 can simply be exposed directly to product sound outputs, for example, by positioning two products behind the subject or behind a screen. Accurate digital sound recordings, however, have many practical advantages in the method of the present invention.

Physiological monitoring apparatus 17 can take a number of different forms, as will be set forth in greater detail hereinafter. Such monitoring apparatus are well known in the field of biofeedback studies and can include electromyography, electrocardiography and electroencephalography apparatus, as well as respiratory rate sensors. Typically apparatus 17 will include a plurality of sensing transducers or electrodes which are coupled to test subject 21 as well as the physiological monitoring apparatus interface 20, a CPU with associated input device (e.g., keyboard) 22 and a display device 29.

In FIG. 2 subject 21 is shown as he is listening to recorded muffler sounds. Various electrophysiological response transducers are coupled to the subject to enable sensing of his physiological response. Thus, electroencephalograph electrodes or transducers 23 and 24 are affixed to his forehead so as to sense the activity of the left and right forebrain in response to the sound. Transducers 23 and 24 cooperate with a ground electrode, not shown. Heart rate variability transducers 26 are fixed to the subject's ears. A pair of surface electromyographic electrodes, not shown, are mounted to the left trapezius muscle and connected by conductors 25 to an electromyographic monitor. Preferably a second pair of surface electrodes are mounted over the right trapezius muscle and electrically connected to the monitor. A respiratory transducer 28 is mounted to the user just below the lungs, and pulse sensors 30 are mounted on the interior of each arm proximate the wrist.

Thus, as subject 21 listens to a content-free sound output of a product, simultaneous physiological responses of the subject to the sound can be sensed. During this process, the subject should generally minimize physical activity and attempt to assume a relaxed or baseline state. Achieving a baseline or relaxed state can be monitored using the same sensors, and testing of the effect or response of a test subject to a particular sound preferably does not start until the outputs from the various sensing apparatus have stabilized at baseline values. Once stabilized, the recorded sound, or the actual sound, can be commenced and the physiological responses being monitored can be compared to the baseline state or to another sound.

The process of the present invention, therefore, includes the step of sensing at least one physiological response of a subject while the subject listens to an initial content-free sound output. Physiological responses, and particularly stress-induced responses, are monitored by the various transducers and recorded and stored by computer 22 for comparison and/or displayed, as is shown in FIGS. 3 and 4.

The next step in the present process will be to have the test subject listen to a new content-free sound output. This can be accomplished, for example, by changing products or by changing the geometry of the same product. For mufflers, the position of baffles or partitions, or the size or shape of chambers or the presence or absence of sound attenuating packing, such as fiberglass, each can be varied. This can be done, for example, in a prototyping facility, and the sound of the two mufflers of differing geometry, or a single muffler whose geometry has been varied, can be recorded on recording medium 16 for playback by playback device 15 to the subject. For some products, and even to a limited extent for mufflers, this change or variation can be done while the subject listens directly to the sound output from the muffler.

Obviously, it is important to accurate sound response monitoring that the subject does not know which sound the technician believes to be the least stressful or most pleasing. This can be done so that both the technician and the subject do not know which sound comes from which product. By blind testing prejudices, biases and placebo effects will not affect the monitored responses or their interpretation. Sound recordings 16 facilitate such blind testing, as well as achieving a baseline state for many types of products.

After the sound output has been changed, the sensing step is repeated for the new content-free sound output, and the physiological responses for the initial sound output and the new sound output are compared. The comparing step can be done in various manners including side-by-side or superimposed comparison of the graphic traces produced on display 29 by the various transducers.

FIGS. 3 and 4 illustrate a side-by-side comparison between physiological responses of a subject to the sound from two mufflers mounted to the same engine. Pulse rate, respiratory rate and heart rate variability are displayed in FIG. 3, while micro-voltages produced in the left and right trapezius muscles are shown in FIG. 4.

As seen in FIG. 3, output or trace 41 is the respiratory rate of the subject, while output or trace 43 records the pulse rate of the subject. Three dimensional representation 45 is a heart rate variability graph. For outputs or traces 41 and 43, the recorded sound was changed at about position 47, and for the heart rate variability display the sound changed at position 53. Thus, a recording for a first muffler was being listened to at start 46 of output traces 41 and 43, and at position 47 the sound recording changed to a second muffler. Heart rate variability graph 45 starts at axis 48 and moves outwardly or forwardly out of the page or along plane 50 toward changeover point 53 and thereafter to the finish or end 52 of the graph.

As will be seen, the pulse rate changed radically at 49, as did the respiratory trace at 51. The pulse 43 increased, while breathing became more labored, i.e., the amplitude of respiratory trace 41 increased and the frequency slowed. The heart rate variability was relatively uniform between start 48 and the changeover 53 and then rose significantly to finish at point 52.

The heart rate variability graph is a Fourier transform of the beat-to-beat interval in the heart rate and the rate at which the interval changes. The rate at which the interval between heart beats changes allows the technician to infer the rate at which signals are coming from brain to the heart in order to stimulate changes in the heart rate.

The left forebrain responds to events and excitement while the right forebrain issues warnings which become downloaded stress responses to the body, which is preparing itself for "fight or flight." Thus, when the test subject was exposed. to the second muffler sound respiration became less uniform in its frequency and increased in its volume as a result of the downloaded stress response from the brain. Heart rate and heart rate variability both increased. These physiological changes were demonstrable and reproducible so as to become objective. The subject might have told a technician that one muffler or the other subjectively sounded better, but it is objectively clear from these data that the second muffler was not as pleasing, or produced a greater physiological stress response, regardless of the subject's subjective perception of the two sounds and despite the fact that the sound outputs have no intellectual content.

These physiological responses were confirmed by the electromyographic data of FIG. 4. Trace 61 is from the pair of bipolar surface electrodes attached to the right trapezius muscle of the test subject, while trace 63 is from the pair of bipolar surface electrodes attached to the left trapezius muscle of subject 21. The traces begin at 65 and proceed to the right while the first muffler recording is being played. At position 67 the recording of the second muffler takes over, and the mobilized stress response in the trapezius muscles greatly increases, i.e., the micro-voltages generated by these muscles rises rapidly until end 69 of the trace.

The electroencephalograph outputs for the right and left hemispheric brain functions were simply not sensitive or sophisticated enough to produce meaningful data. In experimental laboratories electroencephalography studies are conduction with over 100 scalp-mounted transducers, and it is believed that with more sensing transducers and greater computer power direct measurement of both the brain's pleasure responses to sound stimuli could be made.

The next steps in the present process are to select the physiological response indicating the least stressful or the most pleasing, content-free sound output and select or design the product to produce substantially the selected response. Obviously, in most cases, the sound output from many product designs will be compared, and as the frequency changes become more subtle, the response changes will become less pronounced. Nevertheless, a least stressful or most pleasing sound, or range of equally low stress or equally relatively pleasing physiological responses can be identified by the objective comparison of monitored physiological responses. This information will allow the product engineer or designer to select as between products, or design products, in which the sound output is tailored to the product use.

Physiologically less stressful response for the equipment used were found to be ones in which the amplitude and frequency variance from a relaxed state, or as compared to another sound, is the most uniform and least elevated. Thus, in FIG. 3, pulse rate trace 43 is relatively uniform and has a relatively low amplitude between start 46 and changeover 47, as compared to the trace between changeover 47 and the finish of the trace. The same is true of the respiration trace 41, the heart rate variability graph 45 and the electromyography traces 61 and 63.

The process of the present invention is preferably implemented using a plurality of test subjects 21 so that objective data can be obtained for a reasonably representative population of potential product users. Predictably the physiological responses to content-free sound stimuli will vary from individual to individual, but aberrational data can be discarded and an envelope of typical physiological responses developed and used to design or select products.

Using physiological response sensing apparatus, therefore, allows a product evaluator to test products from various manufacturers and select the least stressful product in terms of its sound output. The designer of a piece of apparatus, such as a muffler for an internal combustion engine, can use the present process and apparatus to vary the geometry or structure of the product and then have the subject listen to the sound output while the physiological responses are sensed. At the same time, or in the lab at another time, spectrographic readings of the sound output can be made so that the designer or product evaluator can better understand the sound components in the complex multi-frequency systems and can understand how geometric changes influence the sound spectrum. Spectrographic measurements of the sound can be combined with sensing of the physiological responses so that the product evaluator or designer can objectively determine which content-free sound output bandwidths are perceived by human users as less stressful, and accordingly, more pleasing. The structure of the muffler or other product, therefore, can then be varied based upon objective criteria to produce frequencies which will be more agreeable to the user, rather than relying upon debatable highly subjective perceptions. Objective physiological response measurements can be made which will enhance and allow the design of content-free sound output from complex sound-producing products, such as internal combustion engines and their mufflers.

The range of applications of the present method or process are substantial and extend well beyond the automotive field. In the automotive field, moreover, mufflers for the ordinary consumer, as well as for the race car driver, can be designed which will have sound outputs which are much more agreeable to listeners without sacrificing performance or attempting to isolate the listener from all sound.

What is claimed is:

1. A process of designing or selecting a product comprising the steps of:

sensing at least one physiological response of a subject while the subject listens to an initial content-free sound output using physiological monitoring apparatus to produce a first output;

repeating the sensing step for a new content-free sound output to provide a second output;

comparing first output for the physiological response for the initial sound output with the second output for the physiological response for the new sound output to determine a response change correlated to a sound change;

selecting the physiological response correlated to the sound producing one of: a less stressful sound output, and a more pleasing sound output; and using the selected physiological response to perform one of: selecting as between products, and designing a product, to produce substantially the selected physiological response.

2. The process as defined in claim 1 wherein, the sensing steps are accomplished by sensing at least one electrophysiological response of the subject to the sound outputs.

3. The process as defined in claim 2 wherein, said selecting step is accomplished by selecting the physiological response indicating the least stressful sound output.

4. The process as defined in claim 1, and the steps of:

repeating said sensing step for a plurality of new sound outputs; comparing the physiological response to each new sound output to previously sensed physiological responses prior to performing said selecting step.

5. The process as defined in claim 1 wherein, said sensing step is accomplished by using an electromyography monitoring apparatus and electrodes coupled to sense micro-voltages produced by a muscle.

6. The process as defined in claim 1 wherein, said selecting step is accomplished by selecting the physiological response which is the most uniform in at least one of amplitude variance and frequency variance.

7. The process as defined in claim 1 and the step of:

changing the sound output between said initial sound output and said new sound output during said sensing step.

8. The process as defined in claim 1 wherein, the sensing step is accomplished while the subject listens to the sound outputs from at least one muffler mounted on the exhaust of an internal combustion engine.

9. The process as defined in claim 8 wherein, said new sound output is produced by changing a physical structure of the muffler.

10. The process as defined in claim 8 wherein, said initial sound output and said new sound output are produced by employing two similar mufflers with one muffler having a changed physical structure relative to the other muffler.

11. The process as defined in claim 8, and determining the sound spectrum makeup of the sound output for both mufflers, and employing the sound spectrum for the selected physiological response to design further mufflers.

12. The process as defined in claim 1 wherein, said sensing steps are accomplished while the subject listens to sequentially played recordings of the sound outputs.

* * * * *